United States Patent [19] [11] 4,070,375
Suzuki [45] Jan. 24, 1978

[54] PROCESS FOR PREPARING 1,4-DIOXAN-2-ONES

[75] Inventor: Shigeto Suzuki, San Franciso, Calif.

[73] Assignee: Chevron Research Company, San Francisco, Calif.

[21] Appl. No.: 711,933

[22] Filed: Aug. 5, 1976

[51] Int. Cl.² ........................................... C07D 319/10
[52] U.S. Cl. .............................. 260/340.6; 260/535 P; 260/635 H; 260/636
[58] Field of Search ...................................... 260/340.6

[56] References Cited

U.S. PATENT DOCUMENTS

| 2,331,993 | 10/1943 | MacDowell et al. | 260/340.6 |
| 3,399,215 | 8/1968 | Brader | 260/340.6 |

*Primary Examiner*—Ethel G. Love
*Attorney, Agent, or Firm*—D. A. Newell; John Stoner, Jr.; W. Keith Turner

[57] ABSTRACT

1,4-Dioxan-2-ones are prepared by contacting carbon monoxide with formaldehyde, a 1,2-glycol, and a catalytic amount of hydrogen fluoride. The products of this reaction are readily converted into diglycolic acids by heating with aqueous caustic in the presence of a nickel catalyst.

10 Claims, No Drawings

PROCESS FOR PREPARING 1,4-DIOXAN-2-ONES

BACKGROUND OF THE INVENTION

This invention relates to the reaction of carbon monoxide with formaldehyde and a 1,2-glycol to obtain cyclic oxoparadioxanes.

Oxoparadioxanes are cyclic compounds containing a 1,4-dioxan-2-one ring

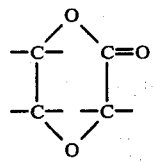

They have a variety of known uses. For example, U.S. Pat. No. 3,280,065, granted Oct. 18, 1966, describes latex stabilization and preservation compositions incorporating a heterocyclic compound containg a 1,4-dioxanone ring. Similarly, U.S. Pat. No. 3,351,485, granted Nov. 7, 1967, describes wood preservative compositions incorporating compounds having a 1,4-dioxanone ring. Also U.S. Pat. No. 2,910,518, granted Oct. 27, 1959, describes separation of aromatic hydrocarbons from a hydrocarbon mixture by extracting with ketodioxane.

Oxodioxanes have previously been isolated from the reaction product of the nickel catalyzed reaction of diethylene glycol and ammonia in a quartz reactor in the presence of hydrogen. Dobrovol'skii, et al; *Zh. Vses. Khim. Obschchest*, 1969, 14(5), 589–90 describe such a process.

Malinovskii, et al; *Ukr. Khim. Zh.*, 1970, 36(6), 592–4 prepared 1,4-dioxan-2-one by cyclizing $Cl(CH_2)_2OCH_2\cdot Co_2H$ with triethylamine and by boiling $O_2N(CH_2)_2O(CH_2)_2OH$ with hydrochloric acid.

SUMMARY OF THE INVENTION

This invention provides a process for preparing 1,4-dioxan-2-ones which comprises contacting carbon monoxide with formaldehyde and a 1,2-glycol in the presence of a catalytic amount of hydrogen fluoride at a temperature of from about 0° C to about 100° C and a carbon monoxide partial pressure of from about 10 psia to about 4000 psia.

In another embodiment, this invention provides a process for preparing diglycolic acids which comprises the steps of (1) contacting carbon monoxide with formaldehyde and a 1,2-glycol in the presence of a catalytic amount of hydrogen fluoride to prepare a 1,4-dioxan-2-one; and (2) contacting the dioxanone product of step (1) with water and, optionally, added base in the presence of a catalytic amount of a dehydrogenation catalyst to prepare a diglycolic acid.

DETAILED DESCRIPTION OF THE INVENTION

The process provided by this invention is founded upon the discovery that, in the presence of a catalytic amount of hydrogen fluoride, carbon monoxide, formaldehyde, and a 1,2-glycol react to prepare a 1,4-dioxan-2-one. The reaction is carried out under moderate conditions of temperature and pressure.

The reaction to form a 1,4-dioxan-2-one is believed to proceed according to the reaction sequence:

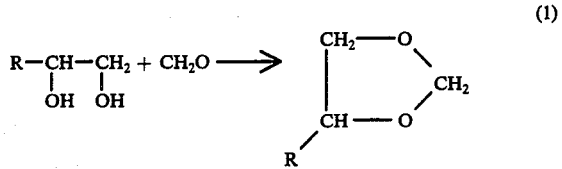

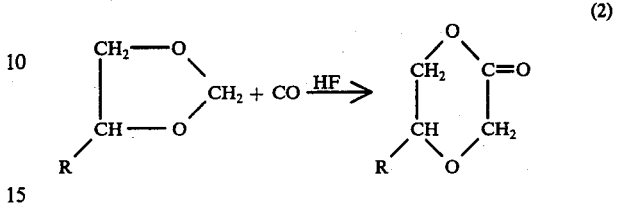

wherein R is selected from the group consisting of hydrogen; and $C_1$ to $C_{20}$ alkyl, cycloalkyl, hydroxyaldyl, aralkyl and alkoxyalkyl. Glycols wherein R is $C_1$ to $C_{20}$ alkyl are preferred for use herein. The reaction is carried out using known processing techniques. Accordingly, the product of step 1, a 4-substituted-1,3-dioxolane, can be contacted directly with carbon monoxide to prepare the final 1,4-dioxan-2-one product.

The 1,2-glycol used in the process is a common diol prepared by a variety of methods. For example, unsaturated compounds can be oxidized by dilute aqueous permanganate and hydrogen peroxide in the presence of osmium tetroxide:

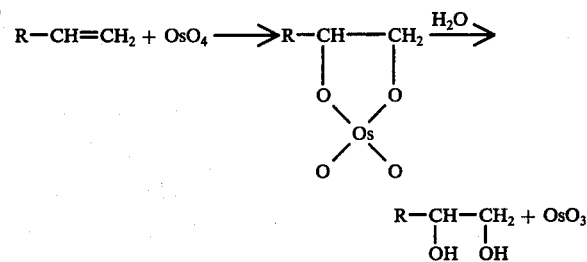

In another method, 1,2-epoxides can be hydrolyzed to 1,2-glycol by either acid or base catalysts. In yet another method, 1,2-dihalides are converted to 1,2-glycols by formation of an intermediate biacetate which is hydrolyzed to the corresponding glycol:

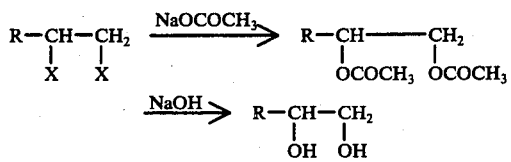

wherein X is a halogen, e.g., Cl.

Representative 1,2-glycols suitable for use in the process of this invention include, for example, ethylene glycol; 1,2-propanediol; 1,2-butanediol; 3-trifluoromethyl-1,2-pentanediol; 5-phenyl-1,2-pentanediol; 3-methoxy propane-1,2-diol; 4-(p-nitrophenyl)-1,2-butanediol; 2-cyclohexyl-1,2-ethanediol; 1,2-octanediol; glycerol and the like.

The reaction is carried out at a temperature of from about 0° C to about 100° C, preferably from about 20° C to about 60° C; and a carbon monoxide partial pressure of from about 10 psia to about 4000 psia, preferably from about 10 psia to about 3000 psia.

Although the preferred source of carbon monoxide is gaseous carbon monoxide as is obtained in synthesis gas, it is also contemplated that carbon monoxide can be formed in situ by a chemical reaction, e.g., by the decomposition of formic acid into carbon monoxide and water.

In producing 1,4-dioxan-2-ones by the process of this invention, the reactants and hydrogen fluoride are fed to the reaction zone at a formaldehyde to 1,2-glycol to hydrogen fluoride mol percent of from about 5–35% formaldehyde, about 5–35% glycol, and from about 40–90% hydrogen fluoride; and the monoxide partial pressure is maintained at from about 10 psia to about 4000 psia. A hydrogen fluoride media is used to catalyze the reaction. Also some water may be present as long as it is not excessive.

In a preferred embodiment, the reaction is carried out at a temperature of about 25° C and a carbon monoxide partial pressure of from about 50 psia to about 2000 psia. Formaldehyde and ethylene glycol are introduced into the reaction zone at a molar ratio of about 1:1. Hydrogen fluoride catalyses the reaction.

Despite the moderate reaction conditions which are used in this process, the reaction runs to completion in commercially reasonable times. In general, it is possible to obtain high conversions in as little time as about 30 minutes. 100% conversions have been obtained in one hour.

The hydrogen fluoride catalyst is readily separated from the reaction product. Since the boiling point of HF is about 19.7° C at one atmosphere, which is considerably more volatile than the reaction products, HF can be easily separated by distillation and recycled to the reaction zone. Any unreacted formaldehyde may also be distilled from the reaction product and recycled to the reaction zone.

The carbon monoxide used in this process can be passed either co-currently or counter-currently to the formaldehyde and glycol reactants. In a preferred system, a synthesis gas comprising carbon monoxide and hydrogen is passed in cascade fashion past the formaldehyde and glycol reactants and hydrogen fluoride catalyst so that the carbon monoxide is reacted out of the upward flowing stream and a purified gas stream of reduced carbon monoxide content is obtained. The purified hydrogen rich gas can be used in various hydrogenation processes. In addition to hydrogen, the carbon monoxide may be diluted with other inert gases, such as nitrogen or carbon dioxide. In these cases the carbon monoxide partial pressure should exceed 10 psia.

The reaction product comprising a 1,4-dioxan-2-one can be purified in several ways. For example, the crude product can be distilled according to conventional methods. Where the 1,4-dioxan-2-one is intended as a feedstock in the preparation of diethylene glycols, the crude product can be contacted with hydrogen in the presence of a hydrogenation catalyst such as copper chromite to prepare a reaction product comprising a diethylene glycol. The diethylene glycol is readily separated by distillation from the hydrogenated product.

As an important feature of this process, it has been found that 1,2-glycols will combine with formaldehyde and carbon monoxide to form 5-substituted-1,4-dioxan-2-ones. The ring position of the substituent is such that, upon cleavage of the ring by hydrolysis, contact with dehydrogenation catalyst forms the substituted diglycolic acid.

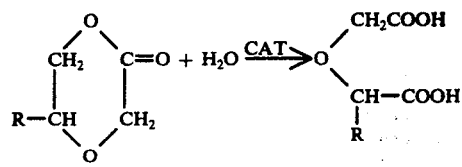

wherein R is defined as above. Thus, in another embodiment, this invention provides a process for preparing diglycolic acids which comprises contacting carbon monoxide with formaldehyde and a 1,2-glycol in the presence of a catalytic amount of hydrogen fluoride to prepare a 1,4-dioxan-2-one; and contacting the dioxanone product with water in the presence of a catalytic amount of a metallic dehydrogenation catalyst.

Hydrolysis of the dioxanone is in many aspects analogous to ester hydrolysis, since the dioxanone ring is in essence a cyclic ester. The hydrolysis can be carried out in an aqueous media under either basic or acidic conditions. Hydrolysis of the dioxanone leads to the formation of the open chain hydroxy acid

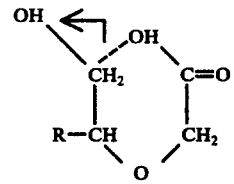

which can be dehydrogenated to form the di-acid

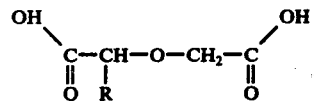

and hydrogen. The usual dehydrogenation catalysts such as Raney nickel, Raney cobalt and platinum or alloys thereof, can be used to catalyze dehydrogenation.

Preferably, hydrolysis and dehydrogenation are carried out in a single step by heating the dioxanone in an aqueous solution with or without an added base such as sodium hydroxide or ammonia in the presence of a dehydrogenation catalyst at a temperature of from about 150° C to about 250° C and a pressure of from about 100 psia to about 500 psia.

The following Examples illustrate the practice of this process. Those familiar with the art will appreciate that various modifications of the procedures used in the Examples are possible.

EXAMPLES

EXAMPLE 1

PREPARATION OF OXOPARADIOXANE

A 300-ml magnetically stirred stainless-steel autoclave was charged with 18.6 grams (0.30 mol) of ethylene glycol, 9.0 grams (0.30 mol formaldehyde) of trioxane and 50 ml of anhydrous hydrogen fluoride. The autoclave was then pressured to 1980 psig with CO at 24° C. The resulting mixture was stirred for 55 minutes, during which time the temperature rose to 29° C. After cooling to room temperature and degassing, the hydrogen fluoride was removed by evaporation and the residual organic layer (30.3 grams) was analyzed by gas chromatography after methanol treatment. The crude product mixture contained about
- 10% unconverted ethylene glycol,
- 10% glycolic acid and
- 80% oxoparadioxane (1,4-dioxan-2-one).

The yield of oxoparadioxane was 85% based on initially employed formaldehyde and almost quantitative based on ethylene glycol reacted.

Another run was carried out in the same manner, except that 18.0 grams (0.60 mol formaldehyde) of trioxane and a CO pressure of 1000 psig were used. In this run, there was 100% conversion of ethylene glycol and formaldehyde. The ethylene glycol conversion and oxoparadioxane yield were almost quantitative. Also, about equimolar amounts of glycolic acid and oxoparadioxane were produced.

In the above procedure when ethylene glycol is replaced with an equivalent amount of propylene glycol the corresponding 5-methyl-1,4-dioxan-2-one is produced.

EXAMPLE 2

PREPARATION OF DIGLYCOLIC ACID

A 200-ml magnetically stirred Monel reactor with attached Grove loader with pressure setting of 300 psig was charged with 2-oxoparadioxane (90% purity) 5.1 grams, sodium hydroxide 8.0 grams water 8.5 grams and Raney nickel 0.7 grams. The mixture was stirred at 215° C and hydrogen evolution practically ceased after 2 hours. Acidification and analysis of the product by gas chromatography showed over 98% conversion of 2-oxoparadioxane with 75 mol percent yield of diglycolic acid.

Another run was carried out in the same manner, except that 0.7 grams of Raney cobalt were used instead of Raney nickel. After 5.5 hours reaction at 225° C, 73% conversion of 2-oxoparadioxane and 93 mol percent yield of diglycolic acid were obtained.

EXAMPLE 3

PREPARATION OF OXOPARADIOXANE

A 300-ml magnetically stirred stainless-steel autoclave was charged with 29.6 grams of 1,3-dioxolane and 50 ml of anhydrous hydrogen fluoride. The autoclave was then pressured to 1060 psig with CO at 8° C. The resulting mixture was stirred for 55 minutes, during which time the temperature rose to 26° C. After degassing and stripping of the hydrogen fluoride, the residue was analyzed by gas chromatography. The conversion of 1,3-dioxolane and yield of 2-oxoparadioxane were 99% and 90.4 mol percent, respectively.

What is claimed is:

1. A process for preparing a 1,4-dioxan-2-one and 5-substituted-1,4-dioxan-2-ones which comprises contacting carbon monoxide with formaldehyde and a 1,2-glycol in the presence of a catalytic amount of hydrogen fluoride.

2. A process according to claim 1 wherein said glycol is ethylene glycol.

3. A process according to claim 1 carried out at a temperature of from about 0° C to about 100° C.

4. A process according to claim 1 carried out at a carbon monoxide partial pressure of from about 10 psia to about 4000 psia.

5. A process according to claim 1 wherein the formaldehyde to glycol molar ratio is about 1:1.

6. A process according to claim 1 wherein the hydrogen fluoride is present at a mol percent of from about 40% to about 90%.

7. A process according to claim 1 wherein said glycol is ethylene glycol, the formaldehyde to glycol molar ratio is about 1:1, the hydrogen fluoride mol percent is from about 40% to about 90%, and the process is carried out at a temperature of from about 20° C to about 60° C and a carbon monoxide partial pressure of from about 10 psia to about 3000 psia.

8. A process according to claim 1 wherein the 1,4-dioxan-2-one is selected from the group consisting of 1,4-dioxan-2-one and 5-substituted-1,4-dioxan-2-ones wherein the substituent is $C_1$ to $C_{20}$ alkyl, cycloalkyl, hydroxyalkyl, aralkyl or alkoxyalkyl.

9. A process according to claim 1 wherein the 1,2-glycol contains from 1 to 22 carbon atoms.

10. A process for preparing 1,4-dioxan-2-ones which comprises contacting carbon monoxide with formaldehyde and a 1,2-glycol in the presence of a catalytic amount of hydrogen fluoride at a temperature of from about 0° C to 100° C and a carbon monoxide partial pressure of about 10 psia to about 4000 psia.

* * * * *